US00PP19670P2

(12) United States Plant Patent
Tonies

(10) Patent No.: US PP19,670 P2
(45) Date of Patent: Feb. 3, 2009

(54) ***ANEMONE* PLANT NAMED 'LITTLE PRINCESS'**

(50) Latin Name: *Anemone hupehensis*
Varietal Denomination: Little Princess

(75) Inventor: Hubertus Josephus Tonies, Noordwijkerhout (NL)

(73) Assignee: Ditoplant Export B.V., Noordwijkerhout (NL)

( * ) Notice: Subject to any disclaimer, the term of this patent is extended or adjusted under 35 U.S.C. 154(b) by 0 days.

(21) Appl. No.: 12/006,217

(22) Filed: Dec. 31, 2007

(51) Int. Cl.
*A01H 5/00* (2006.01)

(52) U.S. Cl. ..... Plt./263.1
(58) Field of Classification Search ..... Plt./263.1
See application file for complete search history.

*Primary Examiner*—Annette H Para
(74) *Attorney, Agent, or Firm*—C. A. Whealy

(57) ABSTRACT

A new and distinct cultivar of *Anemone* plant named 'Little Princess', characterized by its upright and mounding plant habit; freely flowering habit; and pale pink-colored flowers.

1 Drawing Sheet

Botanical designation: *Anemone hupehensis.*
Cultivar denomination: 'Little Princess'.

BACKGROUND OF THE INVENTION

The present invention relates to a new and distinct cultivar of *Anemone,* botanically known as *Anemone hupehensis* and hereinafter referred to by the name 'Little Princess'.

The new *Anemone* is a naturally-occurring whole plant mutation of the *Anemone hupehensis* cultivar Praecox, not patented. The new *Anemone* was discovered and selected by the Inventor as a single flowering plant within a population of plants of the cultivar Praecox in a controlled environment in Noordwijkerhout, The Netherlands during the summer of 2002.

Asexual reproduction of the new *Anemone* by root cuttings in a controlled environment in Noordwijkerhout, The Netherlands since the winter of 2002, has shown that the unique features of this new *Anemone* are stable and reproduced true to type in successive generations.

SUMMARY OF THE INVENTION

The cultivar Little Princess has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Little Princess'. These characteristics in combination distinguish 'Little Princess' as a new and distinct cultivar of *Anemone:*

1. Upright and mounding plant habit.
2. Freely flowering habit.
3. Pale pink-colored flowers.

Plants of the new *Anemone* can be compared to plants of the parent, the cultivar Praecox. Plants of the new *Anemone* differ from plants of the cultivar Praecox primarily in flower color as plants of the cultivar Praecox have dark pink-colored flowers.

Plants of the new *Anemone* can also be compared to plants of the cultivar Party Dress, disclosed in U.S. Plant Pat. No. 13,844. In side-by-side comparisons conducted in Noordwijkerhout, The Netherlands, plants of the new *Anemone* and the cultivar Party Dress differed in the following characteristics:

1. Plants of the new *Anemone* were more uniform than plants of the cultivar Party Dress.
2. Plants of the new *Anemone* had smaller flowers than plants of the cultivar Party Dress.

BRIEF DESCRIPTION OF THE PHOTOGRAPHS

The accompanying colored photographs illustrate the overall appearance of the new *Anemone,* showing the colors as true as it is reasonably possible to obtain in colored reproductions of this type. Colors in the photographs may differ slightly from the color values cited in the detailed botanical description which accurately describe the colors of the new *Anemone.*

The photograph at the bottom of the sheet comprises a side perspective view of a typical flowering plant of 'Little Princess' grown in a container.

The photograph at the top of the sheet is a close-up view of a typical flower of 'Little Princess'.

DETAILED BOTANICAL DESCRIPTION

The aforementioned photographs and following observations, measurements and values describe plants grown in Lancaster, Pa., under commercial practice during the summer in a polycarbonate-covered greenhouse with day temperatures ranging from 21° C. to 38° C. and night temperatures ranging from 18° C. to 29° C. Plants had been growing for about five months when the photographs and description were taken. In the following description, color references are made to The Royal Horticultural Society Colour Chart, 1995 Edition, except where general terms of ordinary dictionary significance are used.

Botanical classification: *Anemone hupehensis* cultivar Little Princess.

Parentage: Naturally-occurring whole plant mutation of the *Anemone hupehensis* cultivar Praecox, not patented.

Propagation:

*Type.*—By root cuttings.

*Time to produce a rooted young plant.*—About 100 days.

*Root description.*—Fibrous; brown in color.

*Rooting habit.*—Freely branching; moderately dense.

Plant description:

*Plant and growth habit.*—Perennial; upright and mounding plant habit. Freely basal clumping habit; about 30 to 40 basal shoots per plant. Vigorous growth habit.

*Plant height.*—About 52 cm.

*Plant diameter.*—About 38 cm.

*Basal shoot length.*—About 2 cm.

*Basal shoot diameter.*—About 8 mm.

*Basal shoot internode length.*—About 4 mm.

*Basal shoot texture.*—Pubescent.

*Basal shoot color.*—147C.

Foliage description:

*Arrangement.*—Alternate, simple.

*Length.*—About 10.6 cm.

*Width.*—About 9 cm.

*Shape.*—Maple leaf-shaped.

*Apex.*—Acute.

*Base.*—Cordate.

*Margin.*—Biserrate.

*Texture, upper and lower surfaces.*—Pubescent.

*Venation pattern.*—Palmate.

*Color.*—Developing foliage, upper surface: Close to 137B. Developing foliage, lower surface: Close to 137C. Fully expanded foliage, upper surface: Close to 139A; venation, 147B. Fully expanded foliage, lower surface: Close to 137C; venation, 147B.

*Petiole.*—Length: About 20 cm. Diameter: About 2 mm. Texture, upper and lower surfaces: Pubescent. Color, upper and lower surfaces: Close to 146B.

Flower description:

*Flower arrangement and habit.*—Single rose-like flowers arranged in dichasial cymes with long peduncles. Freely flowering habit with 13 to 15 flowers and flower buds per inflorescence. Flowers face mostly upright to slightly nodding. Flowers not fragrant.

*Natural flowering season.*—Plants of the new *Anemone* flower in the early autumn in Pennsylvania. Individual flowers last about four to five days on the plant; flowers not persistent.

*Inflorescence height.*—About 23 cm.

*Inflorescence diameter.*—About 10 cm.

*Flower diameter.*—About 3.6 cm.

*Flower length* (*depth*).—About 1.4 cm.

*Flower bud.*—Shape: Spherical. Length: About 1 cm. Diameter: About 1.6 cm. Color: Close to 84C to 84D.

*Petals. Absent.*

*Sepals.*—Quantity/arrangement: About five arranged in a single whorl, radially symmetrical. Length: About 2.1 cm. Width: About 1.4 cm to 2.3 cm. Shape: Obovate to elliptical. Apex: Slightly emarginate. Base: Acute. Margin: Entire; slightly sinnuate. Texture: Glabrous, smooth, satiny. Color: When opening, upper surface: Close to 84D. When opening, lower surface: Close to 84C. Fully opened, upper surface: Close to 194C tinted with close to 186D. Fully opened, lower surface: Close to 194A tinted with close to 186B.

*Peduncles.*—Length: About 24 cm. Diameter: About 3 mm. Aspect: Mostly erect. Texture: Pubescent. Color: 146B.

*Pedicels.*—Length: About 13 cm. Diameter: About 1.5 mm. Aspect: Upright to about 45° from vertical. Texture: Pubescent. Color: 146B.

*Reproductive organs.*—Androecium: Stamen number per flower: About 100. Filament length: About 4 mm. Filament diameter: Less than 1 mm. Filament color: Close to 155D. Anther shape: Oblong. Anther length: About 2 mm. Anther color: 23A. Amount of pollen: None observed. Gynoecium: Pistil number per flower: About 50. Pistil length: About 2 mm. Stigma shape: Rounded. Stigma color: 144B. Style length: Less than 1 mm. Style color: Close to 144B. Ovary color: Close to 144B. Seed/fruit: Seed and fruit development have not been observed on plants of the new *Anemone*.

Garden performance: Plants of the new *Anemone* have been observed to have good garden performance and to be suitable for USDA Hardiness Zones 5 to 9.

Pathogen/pest resistance: Plants of the new *Anemone* have not been observed to be resistant to pests and pathogens common to *Anemone*.

It is claimed:

1. A new and distinct *Anemone* plant named 'Little Princess' as illustrated and described.

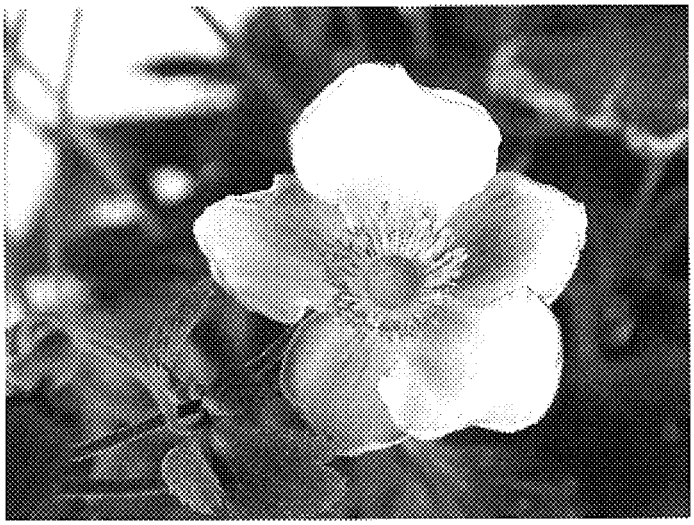
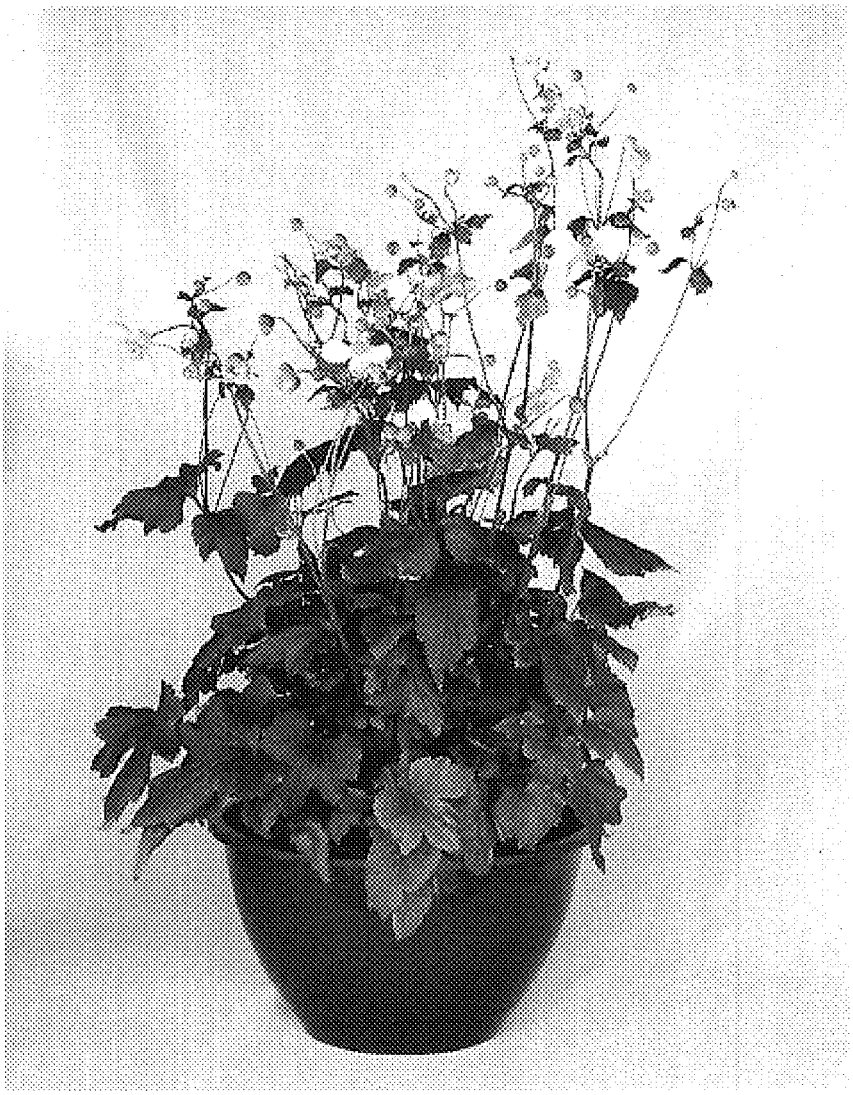

* * * * *